(12) United States Patent
Victor

(10) Patent No.: US 10,478,197 B2
(45) Date of Patent: Nov. 19, 2019

(54) MINIMALLY INVASIVE BONE SPARING ACETABULAR REAMER

(71) Applicant: Greatbatch Ltd., Clarence, NY (US)

(72) Inventor: Gary C. Victor, Wheatfield, NY (US)

(73) Assignee: VIANT AS&O HOLDINGS, LLC, Tempe, AZ (US)

(*) Notice: Subject to any disclaimer, the term of this patent is extended or adjusted under 35 U.S.C. 154(b) by 416 days.

(21) Appl. No.: 15/375,699

(22) Filed: Dec. 12, 2016

(65) Prior Publication Data

US 2017/0164955 A1    Jun. 15, 2017

Related U.S. Application Data

(60) Provisional application No. 62/266,342, filed on Dec. 11, 2015.

(51) Int. Cl.
*A61B 17/16* (2006.01)

(52) U.S. Cl.
CPC ...... *A61B 17/1666* (2013.01); *A61B 17/1659* (2013.01); *A61B 17/1617* (2013.01); *A61B 2017/1602* (2013.01)

(58) Field of Classification Search
CPC . A61B 17/16; A61B 17/1613; A61B 17/1615; A61B 17/1617; A61B 17/1659; A61B 17/1662; A61B 17/1664; A61B 17/1666
USPC .......................................................... 606/81
See application file for complete search history.

(56) References Cited

U.S. PATENT DOCUMENTS

| 5,709,688 | A |   | 1/1998 | Salyer |
| 5,976,148 | A | * | 11/1999 | Charpenet ............... A61F 2/34 606/100 |
| 7,513,899 | B2 |   | 4/2009 | Grim |
| 7,608,076 | B2 |   | 10/2009 | Ezzedine |
| 7,632,276 | B2 |   | 12/2009 | Fishbein et al. |
| 7,850,692 | B2 |   | 12/2010 | White et al. |

(Continued)

OTHER PUBLICATIONS

Extended European Search Report, Application 16203474.8, dated May 15, 2017.

(Continued)

*Primary Examiner* — Eric S Gibson
(74) *Attorney, Agent, or Firm* — Steven J. Grossman; Grossman, Tucker, Perreault & Pfleger PLLC

(57) ABSTRACT

An orthopedic bone cutter for cutting bone and tissue is described. The orthopedic bone cutter comprises a cutting shell and a cutting insert that resides within an opening that extends through the apex region of the shell. A pin and slot mechanism positioned within the shell interior provides for independent axial and rotational movement of the insert within the shell. The shell comprises a partially hemispherical structure having a plurality of outwardly extending and spaced apart shell cutting teeth. The insert comprises an annular sidewall that meets an end wall having a plurality of outwardly extending and spaced apart insert teeth. With the insert at a retracted position within the shell, the bone cutter is rotated in a first direction to cause the shell cutting teeth to cut, for example, an acetabular roof and labrum. Then, rotation of the shell in a second opposite direction causes the shell to stop cutting, but provides for the insert to extend outwardly to cut the acetabular floor and fossa.

30 Claims, 18 Drawing Sheets

(56) References Cited

U.S. PATENT DOCUMENTS

| | | | | |
|---|---|---|---|---|
| 8,052,689 B2* | 11/2011 | Sherry | A61B 17/1666 | 606/79 |
| 8,435,243 B2* | 5/2013 | White | A61B 17/1666 | 606/79 |
| 2007/0276396 A1* | 11/2007 | McCarthy | A61B 17/1666 | 606/81 |
| 2008/0161813 A1* | 7/2008 | Sherry | A61B 17/1666 | 606/81 |
| 2009/0088757 A1* | 4/2009 | Tulkis | A61B 17/1666 | 606/81 |
| 2009/0163921 A1* | 6/2009 | Lechot | A61B 17/1617 | 606/81 |
| 2012/0022539 A1* | 1/2012 | Lualdi | A61B 17/1666 | 606/81 |
| 2012/0191099 A1* | 7/2012 | Victor | A61B 17/1666 | 606/81 |
| 2013/0150860 A1* | 6/2013 | Sidebotham | A61B 17/1666 | 606/81 |
| 2014/0271005 A1* | 9/2014 | Xie | A61B 17/1746 | 408/1 R |
| 2016/0089156 A1* | 3/2016 | Fortin | A61B 17/1666 | 606/81 |
| 2016/0089157 A1* | 3/2016 | Fortin | A61B 17/1666 | 606/81 |
| 2016/0089158 A1* | 3/2016 | Fortin | A61B 17/1666 | 606/81 |

OTHER PUBLICATIONS

"The Hip Resurfacing Handbook", Published by Woodhead Publishing Limited, 2013, p. 326.

* cited by examiner

MINIMALLY INVASIVE BONE SPARING ACETABULAR REAMER

CROSS-REFERENCE TO RELATED APPLICATION

This application claims priority from U.S. Provisional Patent Application Ser. No. 62/266,342, filed Dec. 11, 2015.

FIELD OF THE INVENTION

The present invention relates to the art of orthopedic cutting devices, more particularly, to an orthopedic cutting device designed to remove bone and tissue from the acetabulum.

PRIOR ART

Reamers are devices intended to remove tissue and bone from the human body. Similarly to that of a traditional reamer device, the orthopedic cutting device of the present invention is designed to remove bone and tissue from the cotyloid cavity or acetabulum in preparation for the insertion of a prosthetic cup during hip arthroplasty.

The cotyloid cavity is a cup shaped cavity at the base of the hipbone into which the ball-shaped head of the femur is received (FIG. 15). The acetabulum comprises an acetabulum bone floor that extends to the acetabular roof, the bone structure that resides along the upper portion of the cotyloid cavity. The acetabular fossa, a depressed area having a relatively thin bone structure, resides about the center of the acetabular floor. The acetabular labrum, a ring of fibrous cartilage, resides along the outer perimeter of the cotyloid cavity.

Traditional prior art acetabular reamers, such as the one disclosed in U.S. Pat. No. 5,709,688 to Salyer, are generally constructed having a rigid hemispherical shell structure with a continuous hemispherical surface. A plurality of spaced apart teeth, arranged in the same direction, outwardly extend from the shell exterior. The hemispherical structure is suited to create a cavity within the acetabulum which receives a prosthetic cup. Prosthetic cups generally have a curved exterior surface that is inserted into the cotyloid cavity.

During a traditional total hip arthroplasty procedure, a series of prior art reamers are used to form a hemispherically shaped cavity within the acetabulum. The series of prior art reamers of increasing diameter are typically used to gradually form a hemispherical cavity, reaming from the acetabular floor and fossa outwards to the acetabular labrum until a desired diameter is reached. Prior art orthopedic reamers are typically fabricated as modular units that are sold in a set of an array of diameters. These reamer tool sets are generally manufactured with reamer cutting heads providing bore sizes ranging from about 36 mm to about 80 mm in 1 mm increments sometimes totaling over 45 sizes. Since it is desirable to achieve a close prosthetic fit, a wide array of reaming tools of varying sizes are required to be on hand to provide the most precise cut and optimum bore diameter.

The rigid hemispherical shape of prior art reamers causes the hemispherical cavity to gradually be formed of increasing diameter from the acetabular fossa at the center of the acetabular floor outwards to the acetabular roof. Each time a different reamer is inserted, the reamer apex contacts and abrades the acetabular floor and fossa. Such a procedure is believed to remove excessive bone from the acetabular fossa, thus resulting in a reamed acetabulum having reduced strength and rigidity. In addition, the insertion and removal of multiple prior art reamers may potentially lead to infection. Furthermore, the procedure of inserting and removing multiple prior art reamers is potentially traumatic to the body.

The present invention addresses these potential problems by providing a bone cutter that is configured to ream the cotyloid cavity with one device. In contrast to prior art reamers, the bone cutter of the present invention is designed to ream the acetabular roof and acetabular labrum prior to significantly reaming the acetabular floor and acetabular fossa. Therefore, abrasion to the acetabular floor and fossa is reduced, thus resulting in the preservation of more of the acetabular floor and fossa bone structure. As a result, the bone structure of the reamed acetabulum has greater strength and rigidity in comparison to an acetabulum that is reamed by the prior art procedure with the prior art reamers. Furthermore, since the bone cutter of the present invention eliminates the need to introduce and remove multiple prior art reamers, the risk of infection and trauma is minimized.

Many minimally invasive prior art reamers have been designed in an attempt to minimize surgical trauma to the patient. Among these prior art reamer designs is the device disclosed in U.S. Pat. No. 7,850,692 to White et al., which is assigned to the assignee of the present invention and incorporated herein by reference. White discloses an acetabular reamer having a reduced "lemon wedge shaped" profile so that it can pass through an incision of a reduced opening size. However, in contrast to the bone cutter of the present invention, the acetabular reamer of White comprises a fixed rigid reamer shell that necessitates the use of multiple reamer devices to create a hemispherical cavity of a desired diameter. Furthermore, the rigid partial hemispherical design may cause additional abrasion of the acetabular fossa and floor as the apex of the multitude of increasingly large reamers come into contact with the acetabular floor surface.

Another prior art acetabular reamer is disclosed in U.S. Pat. No. 7,608,076 to Ezzedine, which is assigned to the assignee of the present invention and incorporated herein by reference. Ezzedine discloses a collapsible surgical reamer having a hinge along its rotating axis. While the collapsed configuration allows for the device to pass through a minimally invasive incision, the Ezzedine device must be in an unfolded configuration to ream bone and tissue. Thus, the Ezzedine reamer comprises a rigid hemispherical shape having teeth that extend from the hemispherical structure when used within the body. In addition, similar to the other prior art reamer devices, multiple reamers of increasing diameters are required to be inserted and removed from the body to create a cavity of a desired diameter. Thus, the rigid hemispherical structure of the Ezzedine reamer may cause additional abrasion to the acetabular floor and fossa during a procedure which may potentially cause the acetabulum to become less rigid.

Yet another embodiment of an acetabular reamer is disclosed by Sherry et al. in U.S. Pat. No. 8,052,689, which is assigned to the assignee of the present invention and incorporated herein by reference. Sherry discloses an acetabular reamer having a truncated cutting shell that is constructed without an apex. The omission of the apex from the reamer shell allows for the reaming of the acetabular roof and acetabular labrum without contacting the acetabular fossa. However, in order to form a full hemispherical cavity within the acetabulum, the Sherry device must be rocked in a back and forth manner for the cutting teeth to contact the acetabular floor region. Such a rocking motion is not preferred as this may not produce a true hemispherical cavity. Furthermore, the rocking motion of the reamer within the body may aggravate and traumatize surrounding tissue.

The '689 to Sherry et al. patent discloses an alternate embodiment comprising a cap or plate that is positioned over the apex opening. As disclosed by Sherry, the cap or plate is stationary, but separately attached to the shell. Thus, in order to attach the cap or plate, the shell must either be removed from the body or manipulated by the surgeon within the body. In either case, the removal and insertion or the manipulation of the shell within the body to attach the apex cap may cause additional trauma or result in infection to the patient.

In contrast to the prior art reamer device, the bone cutter of the present invention comprises a bone cutting insert that extends and retracts from within an opening that extends through the reamer shell. In addition, the bone cutter of the present invention is configured such that the insert is capable of rotational and axial movement independent of the reamer shell. Thus, when the insert is retracted within the reamer shell, the bone cutter is configured to ream the acetabular labrum and roof. The acetabular fossa or floor may then be reamed by outwardly extending the insert from within the reamer shell without removing the bone cutter from the body. Furthermore, the retracted configuration of the bone cutter of the present invention provides for insertion within a minimally invasive incision.

Thus, the present invention provides a reamer that incorporates design features which address various limitations of the prior art. The features of the bone cutter of the present invention enable the reaming of the acetabular roof and the acetabular floor in separate steps without removal of the device from the body, thus more of the bone structure of the acetabulum preserved while minimizing patient trauma and infection.

SUMMARY OF THE INVENTION

The present invention is an orthopedic cutting device designed to cut and remove tissue and bone material. The device is designed to efficiently remove tissue and bone from the cotyloid cavity for the insertion of an orthopedic implant.

In an embodiment, the bone cutter comprises a reamer shell and a reamer insert that resides within an opening that extends through the apex of the reamer shell. The insert is capable of independent axial and rotational movement within the shell opening. The reamer shell is preferably of a partially hemispherical structure comprising a plurality of spaced apart shell teeth, each having a tissue cutting surface that extends outwardly from the reamer shell exterior surface. The insert preferably comprises an annular sidewall that meets an insert end wall that comprises a plurality of spaced apart insert cutting teeth having a tissue cutting surface.

In an embodiment, the insert rides within a pin and slot mechanism that is positioned within the shell interior. This pin and slot mechanism provides axial and rotational movement of the insert with respect to the shell. In an embodiment, the insert is positioned within a collar that is secured within the reamer interior. The collar comprises an annular sidewall having a slot extending to a groove formed at least partially within the collar sidewall interior surface. A pin extending from the insert sidewall is received within the collar slot and rides therewithin. In an alternate embodiment, the insert is positioned within a collar that is secured within the reamer interior. The collar comprising an annular sidewall having at least one pin that extends outwardly from the collar sidewall interior surface. The insert comprising an insert sidewall having a slot extending to a groove is formed at least partially within the insert sidewall exterior surface. The pin extending from the collar sidewall interior surface is received within the insert slot and rides therewithin.

When the insert is in a retracted position the bone cutter is configured to ream the acetabular roof. In addition, the retracted configuration provides a low profile orientation that helps allow for the insertion of the reamer through a minimally invasive incision. When the insert is in an extended position, the bone cutter is configured to ream the acetabular floor. Thus, the bone cutter of the present invention provides for the separate reaming of the acetabular roof and floor without the need to remove the device from the body.

DETAILED DESCRIPTION OF THE INVENTION

Figure 1:
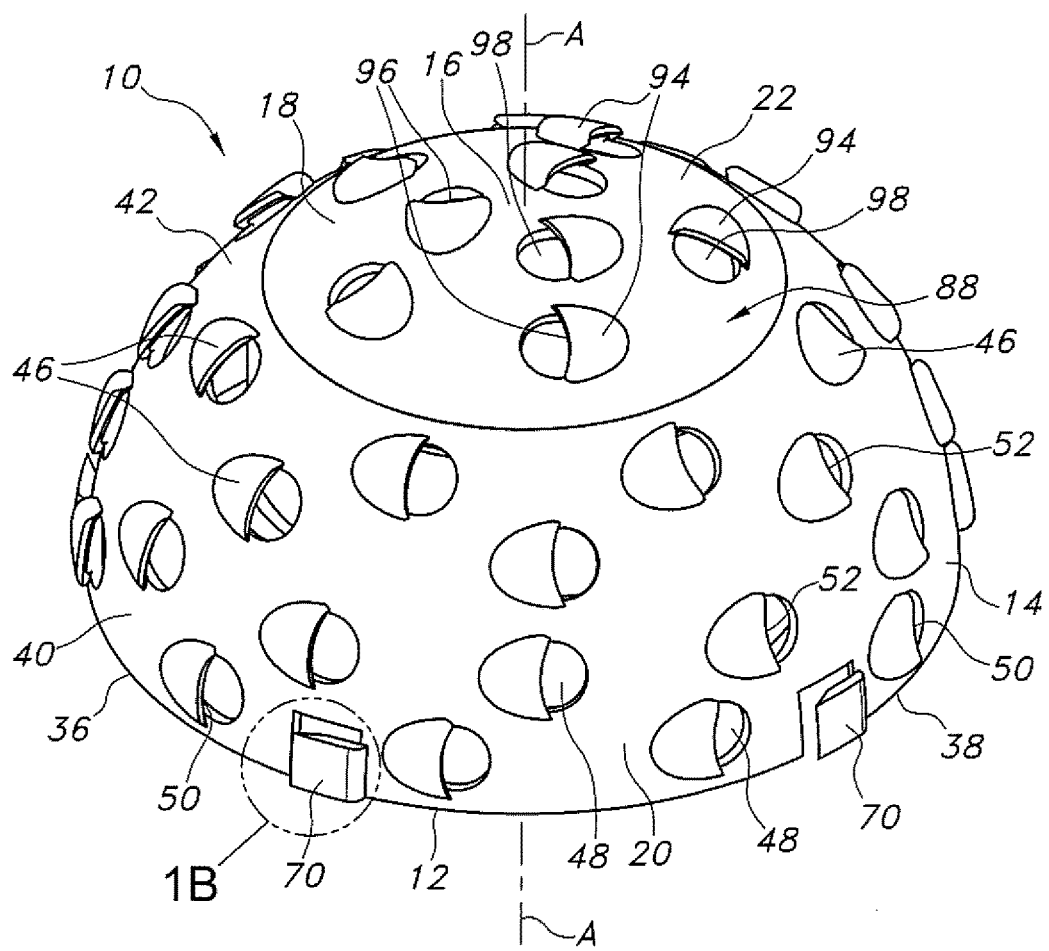
FIG. 1 illustrates a perspective view of an embodiment of the bone cutter of the present invention in an extended position.

Now turning to the figures, FIGS. 1-3, 4A, 4B, and 5 illustrate an embodiment of a bone cutter 10 of the present invention. The bone cutter 10 extends from a bone cutter base 12 at a proximal end 14 to an apex 16 at a distal end 18. An imaginary rotational axis A-A extends through the apex 16. In an embodiment, the bone cutter 10 comprises a reamer shell 20, and a reamer insert 22. Both the reamer shell 20 and insert 22 are configured to cut bone and tissue. In an embodiment, the reamer insert 22 is positioned within an opening 24 (FIG. 6) that extends through a thickness of the shell 20 adjacent to the apex 16.

The insert 22 is designed to rotate either in a clockwise or counter-clockwise direction independent of the reamer shell 20 within the opening 24. In addition, the insert 22 is configured to move in an axial direction along the rotational axis A-A within the shell opening 24. The shell 20 is configured to ream the acetabular roof and labrum while the movable bone cutting insert 22 enables independent reaming of the acetabular floor and fossa. The bone cutter 10 of the present invention thus eliminates the need to remove and insert multiple reamers of increasing diameter during a procedure. Therefore, the possibility that surgical trauma or infection may result is minimized. Furthermore, the insert 22 may be positioned below the shell opening 24 within the shell interior thus providing the bone cutter 10 of the present invention with a low profile that is minimally invasive to insert and remove from the body.

Figure 15:
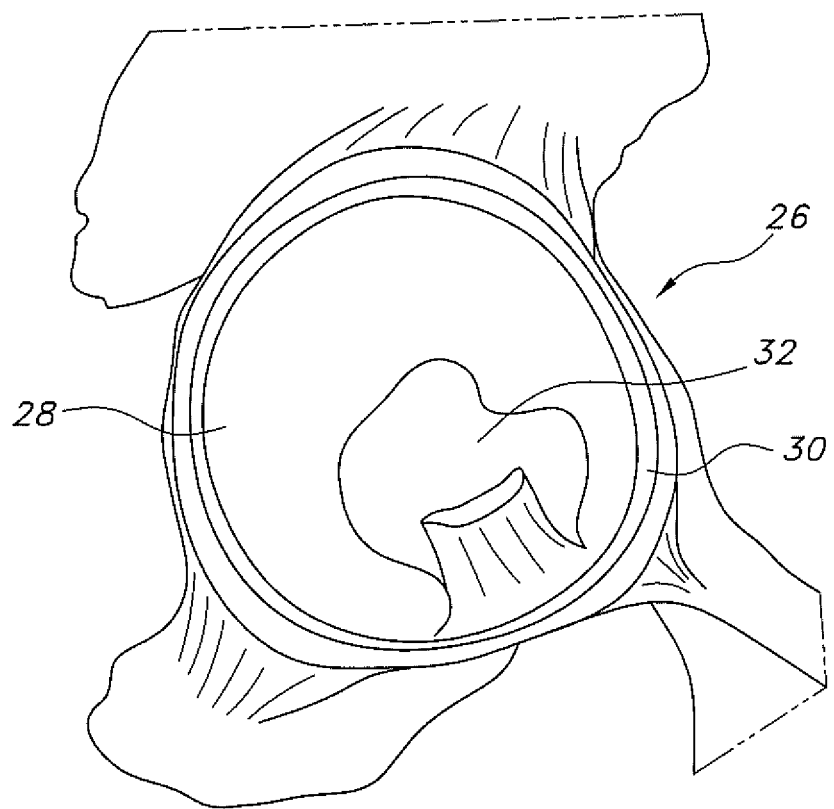
FIG. 15 illustrates an embodiment of the acetabulum.
Figure 16A:
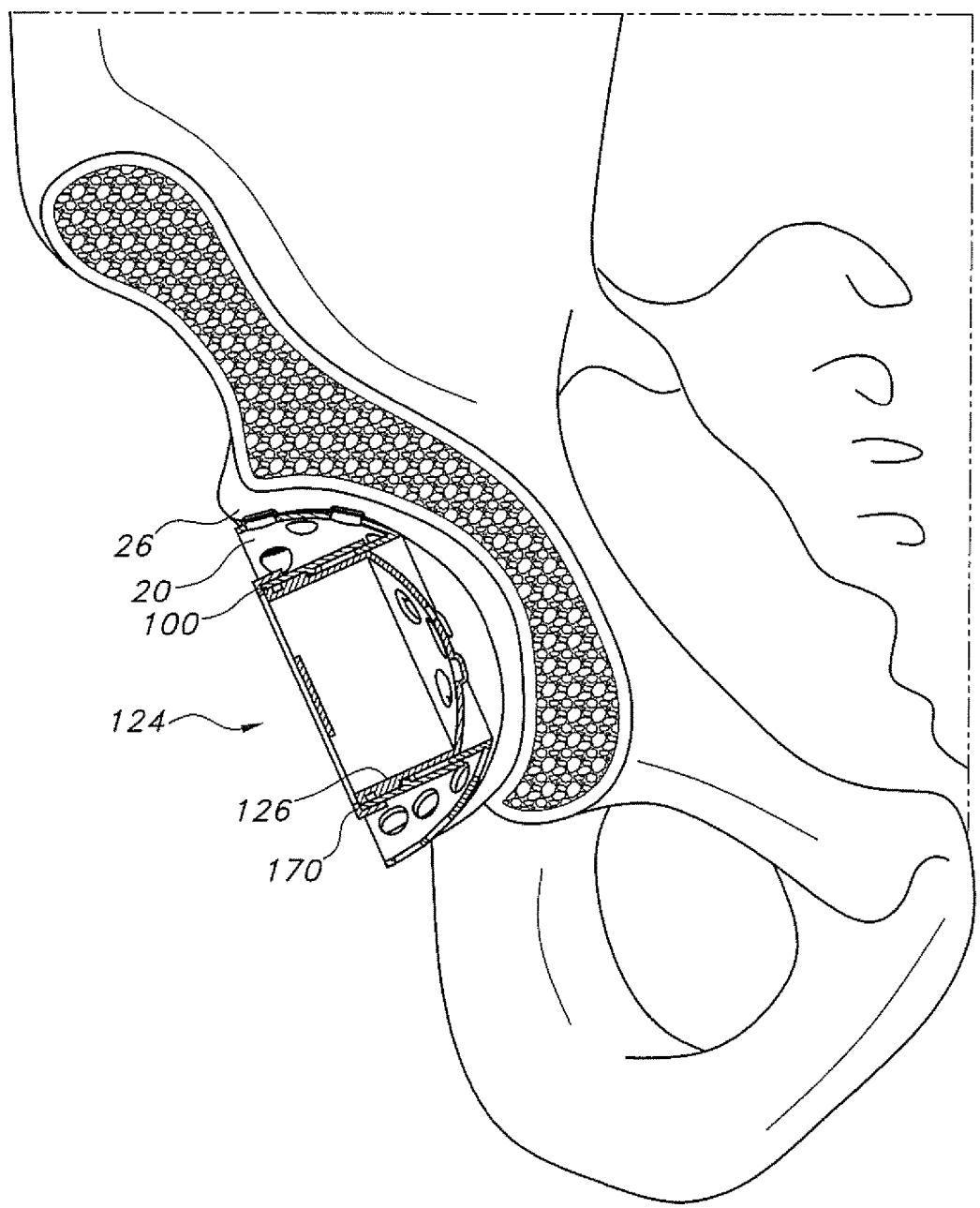
FIG. 16A is a cross-sectional view of an embodiment of the bone cutter of the present invention positioned within the acetabulum with the insert in a retracted position.
Figure 16B:
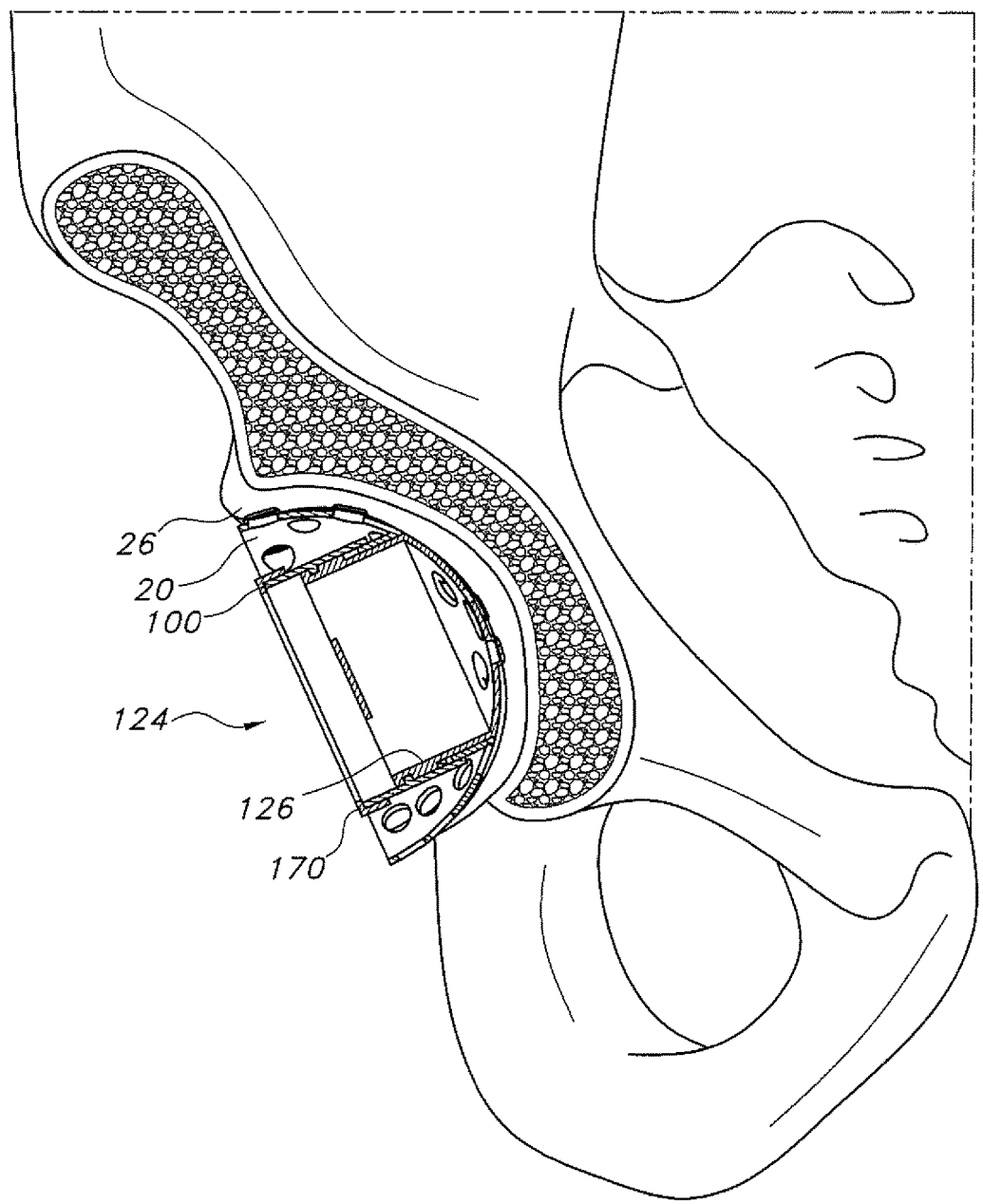
FIG. 16B is a cross-sectional view of an embodiment of the bone cutter of the present invention positioned within the acetabulum with the insert in an extended position.

In the case of reaming the acetabulum 26 during a hip replacement procedure as shown in FIGS. 15, 16A, and 16B, the retractable reamer insert 22 allows for the reaming of the acetabular roof 28 and acetabular labrum 30 prior to the reaming of the acetabular fossa 32 which resides within the acetabular floor. As discussed by K De Smet et al. on page 326 of, *The hip resurfacing handbook: A practical guide to the use and management of modern hip resurfacings,* 2013, reaming the acetabular labrum 28 prior to the acetabular fossa 30 during a hip replacement surgical procedure is beneficial as it preserves more of the acetabulum bone structure.

Figure 6:
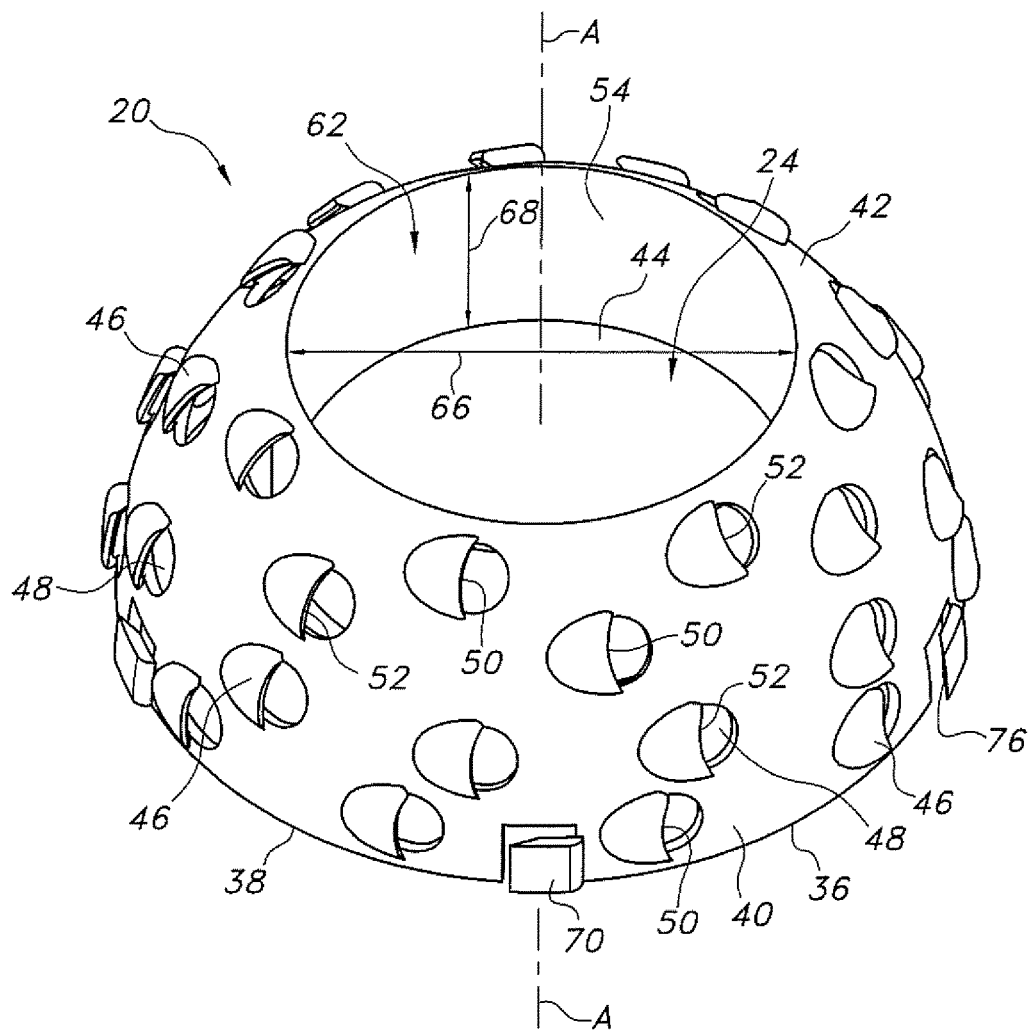
FIG. 6 illustrates a perspective view of an embodiment of the reamer shell component of the bone cutter of the present invention.
Figure 7:
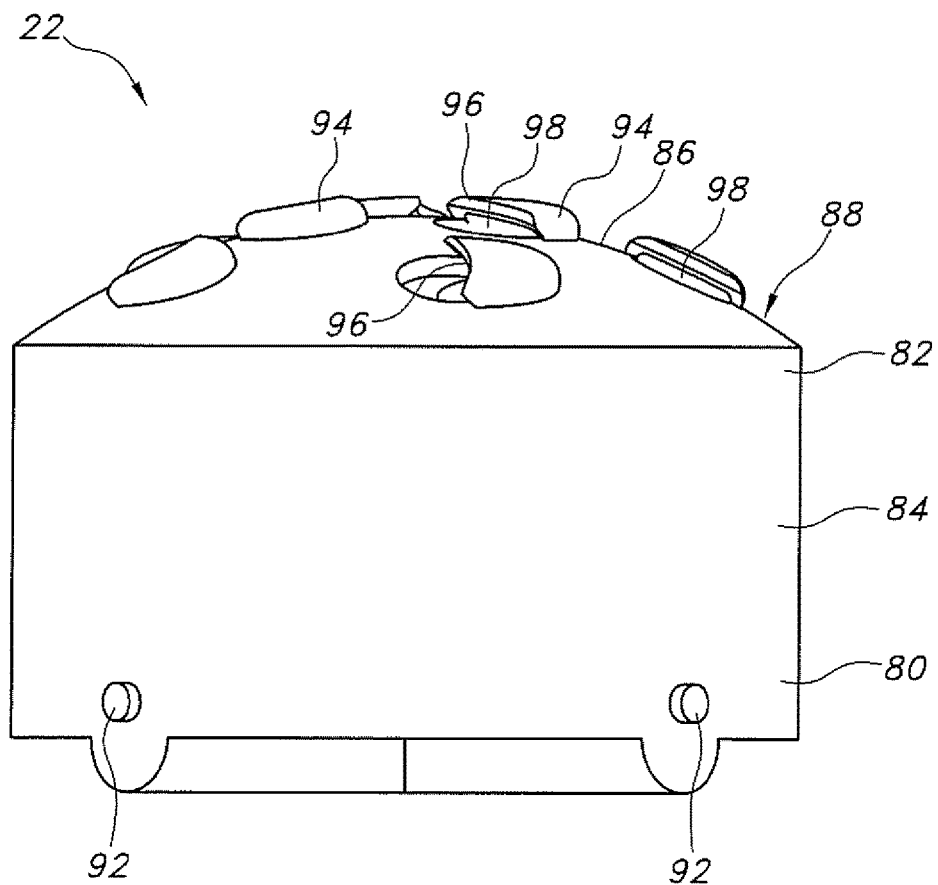
FIG. 7 illustrates a perspective view of an embodiment of an insert component of the bone cutter of the present invention.

FIG. 6 illustrates an embodiment of the reamer shell 20. As shown, the reamer shell 20 comprises a sidewall 34 having a curvature comprising a partial hemispherical shape that extends from a shell base 36 having a base edge 38, that defines a shell base perimeter at a shell proximal end 40. The sidewall 34 extends from the base 36 towards an intermediate edge that defines an intermediate perimeter at a shell distal end 42. The intermediate perimeter is located on an imaginary intermediate plane that is spaced from and positioned between the imaginary apex 16 and the base edge 38. The intermediate perimeter defines the opening 24 having a region 44 that radially extends from the imaginary rotational axis A-A at the bone cutter apex 16. In an embodiment, the base perimeter is greater than the intermediate perimeter.

The shell 20 preferably comprises a plurality of spaced apart reamer teeth 46. Each tooth 46 is formed from the reamer sidewall 34 that outwardly extends from the reamer shell exterior surface. In addition, each of the plurality of reamer shell teeth 46 comprises a tooth opening 48 that extends through the thickness of the shell sidewall 34. The tooth opening 48 allows for the removal of tissue debris during a reaming surgical procedure. A tissue cutting surface 50 is formed at a distal end 52 of each of the plurality of teeth 46 extending outwardly from the reamer shell exterior surface and positioned over the respective tooth opening 48.

In an embodiment, the plurality of reamer shell tissue cutting surfaces 50 is arranged in either a clockwise or counter-clockwise orientation about the rotational axis A-A.

As illustrated in FIGS. 4A, 4B, 5, and 6, the reamer shell 20 comprises a flange 54 having a flange distal end 56 that extends from the intermediate perimeter to a flange proximal end 58 positioned within the shell interior. In an embodiment, the flange 54 comprises a flange sidewall 60 constructed in an annular shape that extends circumferentially about the rotational axis A-A. In an embodiment, the flange sidewall 60 comprises a flange thickness that extends between opposed interior, and exterior flange sidewall surfaces 62, 64. In a preferred embodiment, the flange sidewall 60 defines the intermediate perimeter of the shell opening 24 having an interior diameter 66 that extends between diametrically opposed flange sidewall interior surfaces 62, perpendicular to the rotational axis A-A. The flange interior diameter 66 is preferably dimensioned to receive the reamer insert 22. In a preferred embodiment, the interior flange diameter 66 may range from about 1 cm to about 10 cm. In addition, the flange sidewall 60 has a length 68 that extends in a proximal direction from the flange distal end 56 at the shell opening 24 to the flange proximal end 58. In a preferred embodiment, the length 68 of the flange sidewall 60 may range from about 1 cm to about 5 cm.

Figure 1B:
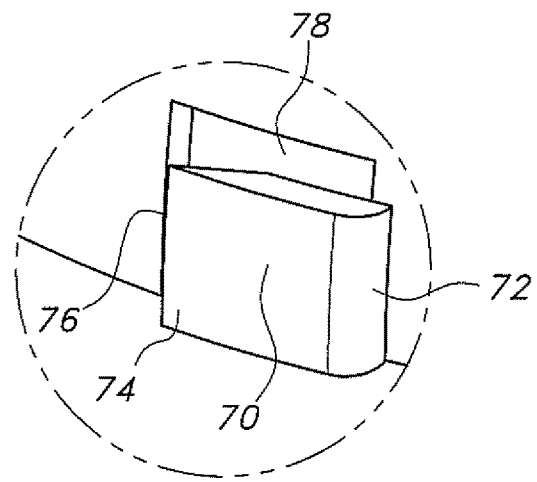
FIG. 1B is an enlarged view of an embodiment of a reamer shell anchor.
Figure 2:
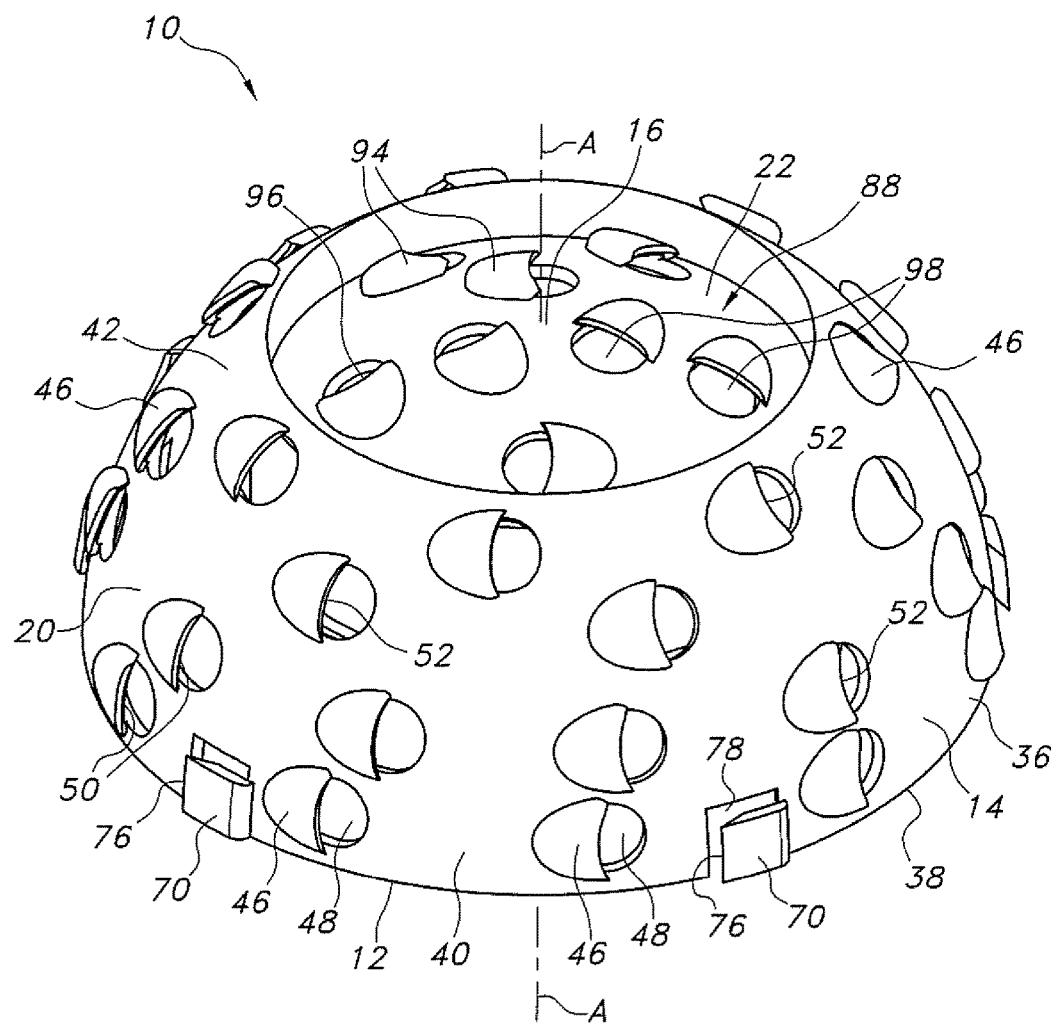
FIG. 2 shows an embodiment of the bone cutter of the present invention in a retracted position.
Figure 3:
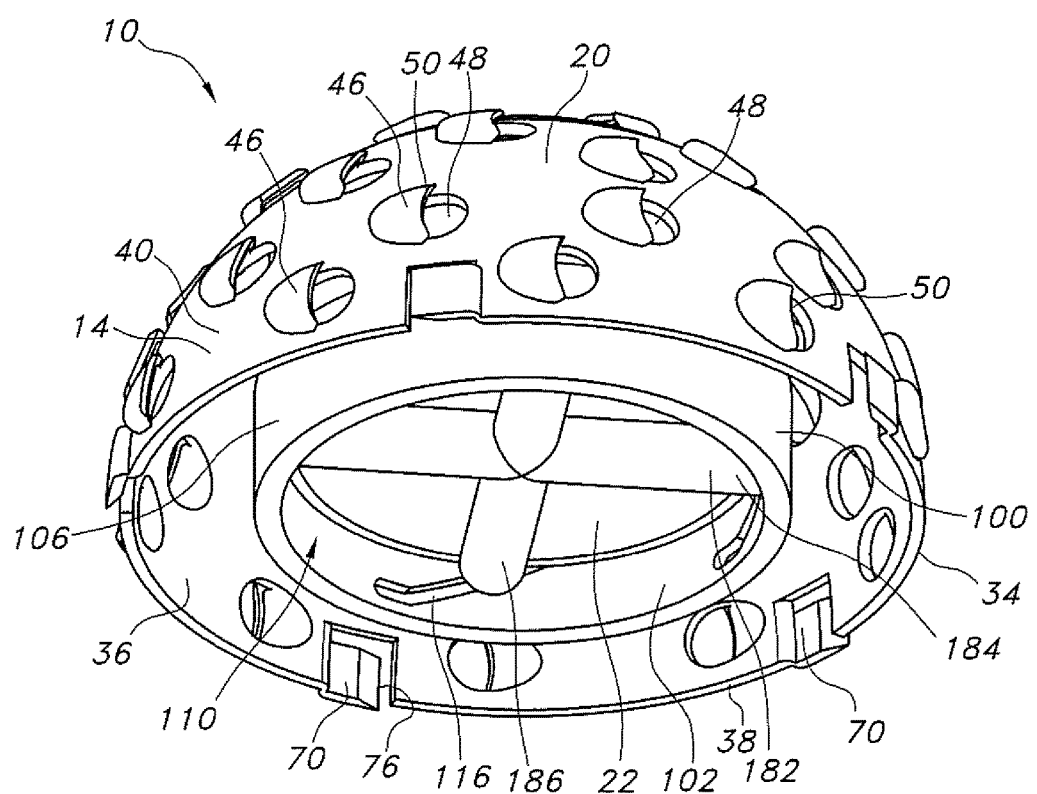
FIG. 3 illustrates an embodiment of the proximal end of the bone cutter of the present invention.

In an embodiment, illustrated in FIG. 1B, the reamer shell 20 comprises at least one anchor 70 that is positioned at the reamer shell base 36. As shown, the anchor 70 extends outwardly from an anchor proximal end 72 at the reamer shell exterior surface to an anchor distal end 74 having an anchor tissue cutting surface 76. As shown in FIG. 1B, the anchor distal end 74 is positioned over an anchor opening 78 that extends through the thickness at the reamer shell base 36. The anchor opening 78 provides space for the flexure of the anchor distal end 74. In addition, the anchor opening 78 allows for the entry of bone or tissue to thereby help secure the shell 20 thereto. In a preferred embodiment, the at least one anchor 70 is configured to embed within surrounding tissue or bone thereby, temporarily immobilizing the reamer shell 20, and thus, allowing for independent rotation of the reamer insert 22 with respect to the reamer shell 20.

In a preferred embodiment, the anchor tissue cutting surface 76 is oriented in an opposite direction as the tissue cutting surface 50 of the reamer shell cutting teeth 46, about the rotational axis A-A. This preferred anchor orientation allows for the shell 20 to ream bone and tissue without causing the anchor 70 to become embedded within tissue or bone. For example, an exemplary bone cutter is configured with the reamer shell teeth 46 oriented in a clockwise direction and the anchor tissue cutting surface 76 oriented in the opposite, counterclockwise direction about the rotational axis A-A. Thus, rotation of the shell 20 in the clockwise direction enables the shell 20 to ream bone and tissue without causing the anchor 70 to become embedded within surrounding bone or tissue. Rotation in the opposite, counter-clockwise direction about the rotational axis A-A, however, causes the anchor 70 to become embedded within surrounding tissue or bone, thereby immobilizing the reamer shell. Subsequent rotation of the shell 20 in an opposite direction, i.e., clockwise direction about rotational axis A-A, causes the anchor 70 to become dislodged from the surrounding tissue and bone. In an embodiment, immobilizing the reamer shell 20 allows for independent reaming of tissue and bone by rotation of the insert 22.

Figure 4A:
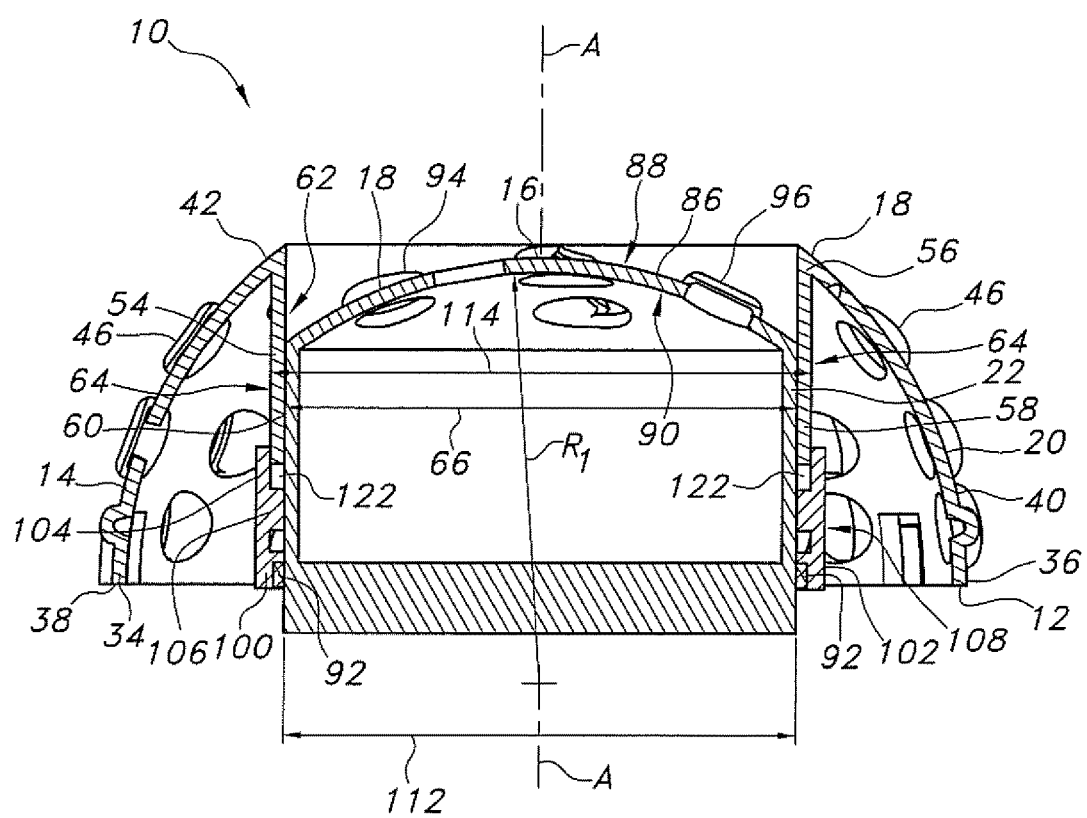
FIG. 4A is a cross-sectional view of the embodiment of the bone cutter of the present invention illustrated in FIG. 1 with the insert in a retracted position.
Figure 4B:
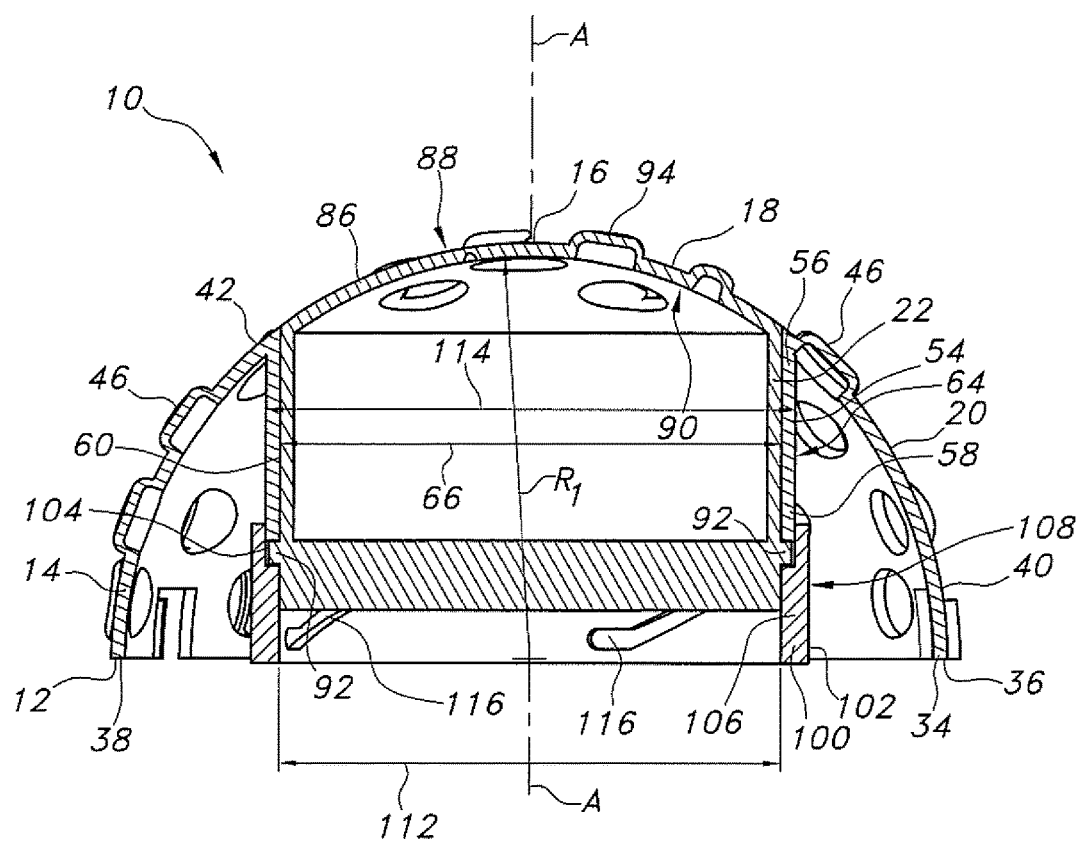
FIG. 4B is a cross-sectional view of the embodiment of the bone cutter of the present invention illustrated in FIG. 1 with the insert in an extended position.
Figure 5:
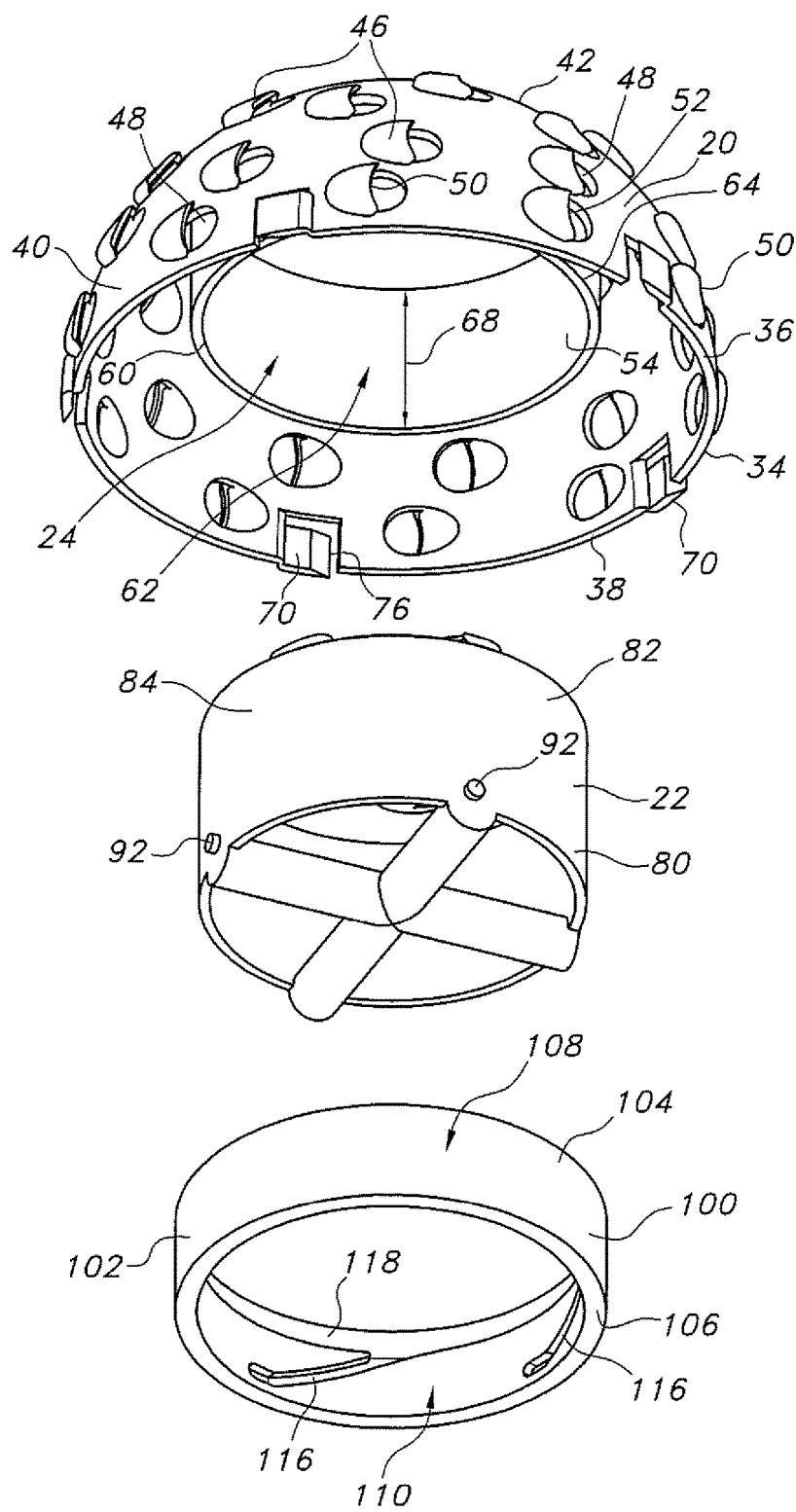
FIG. 5 is an exploded view of the embodiment of the bone cutter of the present invention shown in FIG. 1.

FIGS. 4A and 4B illustrate an embodiment of the reamer insert 22 that is positioned within the reamer shell opening 24. As shown, the reamer insert 22 extends from an insert proximal end 80 to an insert distal end 82. The reamer insert 22 comprises an insert sidewall 84 (FIG. 7) having an annular shape that meets a partial hemispherically shaped insert end wall 86 having opposed distal and proximal end wall surfaces 88, 90. In a preferred embodiment, the insert 22 is positioned within the reamer shell opening 24 with the insert distal end 82 oriented towards the apex 16 along the rotational axis A-A. As illustrated in FIGS. 4A, 4B, 5, and 7, at least two pins 92, outwardly extend in an opposing orientation from the exterior surface of the insert sidewall 84. As shown, four pins 92 outwardly extend from the insert sidewall exterior surface. In a preferred embodiment, the four pins 92 are positioned a distance spaced equally apart at the proximal end 80 of the insert 22.

In an embodiment, the insert end wall 86 comprises a plurality of spaced apart insert teeth 94, each tooth having a tissue cutting surface 96. In an embodiment, each of the plurality of reamer insert teeth 94 is formed from the insert end wall 86 that outwardly extends from the insert end wall distal surface and provides for cutting a hemispherically shaped cavity within the acetabulum. In addition, each of the plurality of insert teeth 94 comprises a tooth opening 98 that extends through the thickness of the insert end wall 86. The opening 98 allows for the removal of tissue debris during a reaming surgical procedure. In an embodiment, the tissue cutting surface 96 is formed at the distal end of each of the teeth 94 extending outwardly from the insert end wall distal surface 88 and is positioned over a respective tooth opening 98. In an embodiment, the plurality of tissue cutting surfaces 96 of the reamer insert teeth 94 are oriented about the rotational axis A-A in an opposite direction to that of the tissue cutting surfaces 50 of the reamer shell teeth 46. For example, if the tissue cutting surfaces 50 of the reamer shell teeth 46 are oriented in a clockwise direction about the rotational axis A-A, the tissue cutting surfaces 96 of the insert teeth 94 are preferably oriented in the opposite, counter-clockwise direction about the rotational axis A-A. Furthermore, the tissue cutting surface 76 of the at least one anchor 70 is oriented in the same direction as the tissue cutting surfaces 96 of the insert teeth 94.

In an embodiment, the insert end wall 86 may have a curved construction. As illustrated in FIGS. 1, 2, 4A, 4B, and 7, the insert end wall 86 preferably comprises a convex structure that outwardly extends in a distal direction. The curvature of the insert end wall 86 allows for the insert 22 to ream a cavity having a curved surface. In an embodiment, the distal surface 88 of the insert end wall 86 may comprise a convex structure having a radius of curvature $R_1$ (FIGS. 4A and 4B) that ranges from about 1 cm to about 5 cm. In a preferred embodiment, when the insert 22 is in an extended position, such that the insert cutting teeth 94 are positioned above the shell opening 24, the curvature of the insert distal end 82 forms the bone cutter apex 16.

In an embodiment, as shown in FIGS. 4A, 4B, 5, 8, and 9, the bone cutter 10 comprises a collar 100 that connects the reamer insert 22 to the reamer shell 20. As illustrated, the collar 100 has a collar proximal end 102 spaced from a collar distal end 104. In an embodiment, the collar 100 comprises a sidewall 106 having a collar sidewall thickness that extends between opposed exterior and interior sidewall surfaces 108, 110. The collar 100 is preferably configured in an annular shape that defines a collar opening with an interior diameter 112 that extends between opposed interior collar sidewall surfaces 110 perpendicular to the rotational axis A-A. In an embodiment, the collar interior diameter 112 is less than an outer diameter 114 of the flange 54. In an embodiment, the collar 100 is preferably secured to the reamer shell flange 54. As illustrated in FIGS. 4A and 4B the collar 100 is positioned at the flange proximal end 58 such that at least a portion of the collar sidewall interior surface is in physical contact with a portion of the flange sidewall exterior surface, thus forming an interference fit therebetween.

Figure 8:
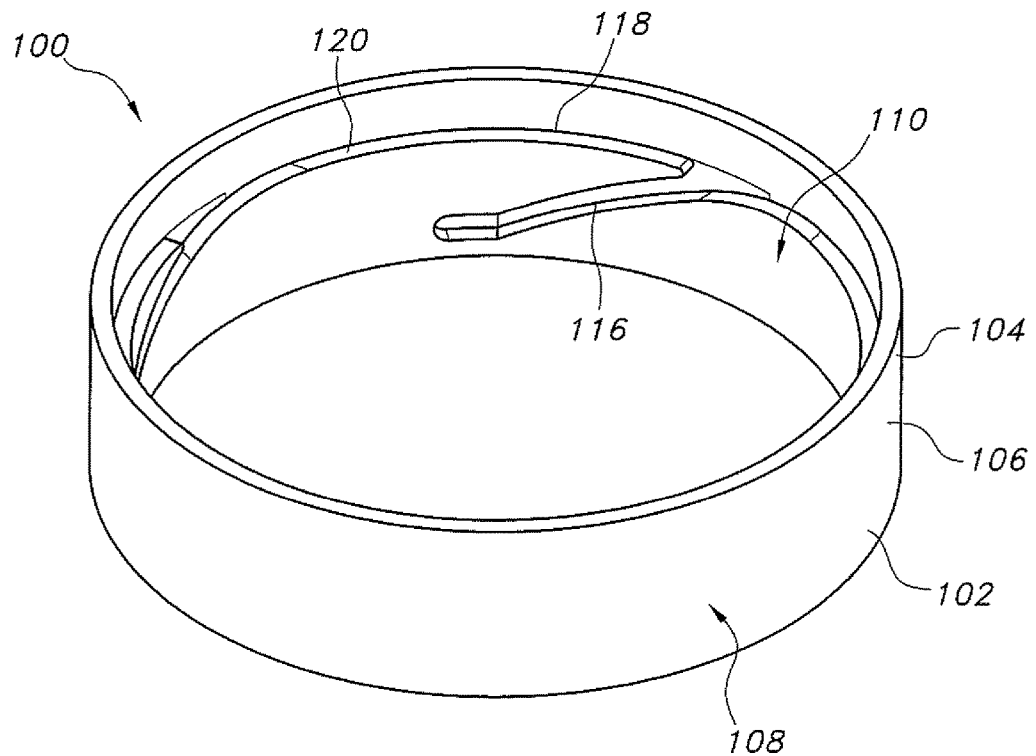
FIG. 8 shows an embodiment of a collar component of the bone cutter of the present invention.
Figure 9:
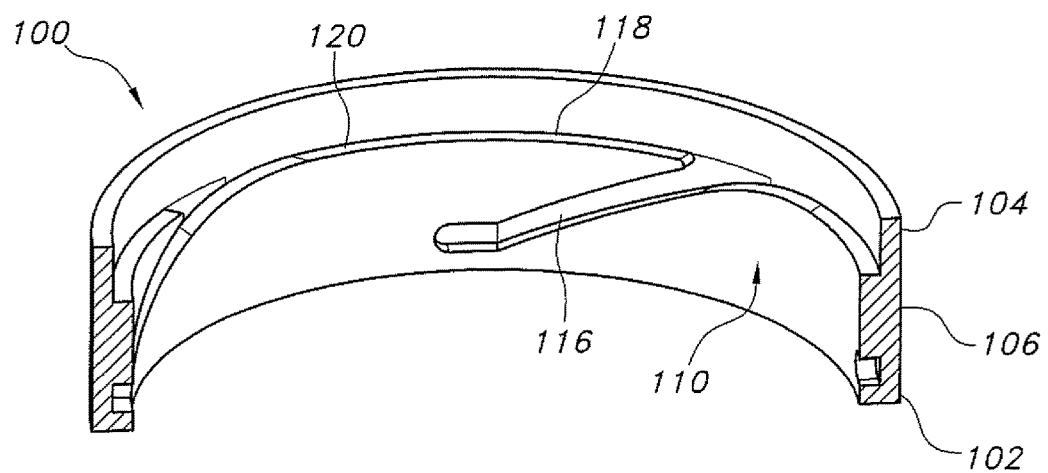
FIG. 9 is a cross-sectional view of the collar component shown in FIG. 8.

In an embodiment, the collar 100 comprises at least two slots 116 (FIGS. 8 and 9), that at least partially extend part-way through the collar thickness from the interior surface 110. The at least two slots 116 are dimensioned to each receive a reamer insert pin 92. As illustrated in FIGS. 8 and 9, the at least two collar slots 116 extend from the collar proximal end 102 to a position spaced from the collar distal end 104. In an embodiment, each of the slots 116 is preferably orientated at an angle with respect to the rotational axis A-A. In a preferred embodiment, the slots 116 are oriented in a spiral orientation about the collar sidewall interior surface 110 with respect to the rotational axis A-A.

In an embodiment, as illustrated in FIGS. 8 and 9, the slots 116 extend from the collar proximal end 102 to a groove 118 having a ledge surface 120 positioned at the collar distal end 104. In a preferred embodiment, the groove 118 is formed part-way through the collar thickness from the interior surface 110. The groove 118 extends circumferentially about the annular collar sidewall 106 and rotational axis A-A. The ledge surface 120, provides a track on which the at least two insert pins 92 rotate about the rotational axis A-A within the collar opening. In an embodiment, the groove 118 is connected to the slots 116 such that the pins 92 are capable of riding in and out of a respective slot 116 and then along the ledge surface 120. In an embodiment, the at least two pins 92 ride within a respective slot 116 that are positioned in opposition to each other. In a preferred embodiment, the pins 92 are capable of riding within the slot 116 in a back and forth manner from the collar proximal end 102 to the ledge surface 120 at the collar distal end 104. As the pins 92 ride within a respective slot 116, the insert 22 rotates within the reamer shell opening 24 and travels in either a distal or proximal direction along the direction of the rotational axis A-A. For example, as the insert 22 is rotated in a clockwise direction, the insert may travel in a distal direction until the pins 92 exit their respective slot 116 and ride along the track formed by the groove 118. In a preferred embodiment, the pins 92 can ride along the track formed by the groove 118 so that the insert 22 is capable of 360° rotation. In an embodiment, the insert 22 may be retracted within the reamer shell 20 by rotating the insert in an opposite direction, i.e., counter-clockwise, such that the pins 92 leave the groove 118 to enter and ride within a respective slot 116 traveling in a proximal direction towards the bone cutter base 12, thus, retracting the insert 22 within the reamer shell 20.

In an embodiment, the collar distal end 104 is secured to the reamer shell flange 54 such that rotational movement of the insert 22 within the reamer shell opening 24 is not impeded. In a preferred embodiment, the collar 100 is secured to the flange 54 such that there is a gap 122 (FIG. 4A) between the flange proximal end 58 and the surface 120 of the groove 118. The gap 122 is dimensioned to allow for travel of the pins 92 therewithin. In an embodiment, the collar 100 may be secured to the flange 54 with an adhesive or by welding the collar 100 to the flange 54. The collar 100 may also be secured to the reamer shell flange 54 by a fastener (not shown). In an embodiment, the fastener (not shown) may at least partially extend through the thickness of the sidewalls of the collar 100 and reamer shell flange 54 to thus secure the reamer insert 22 within the shell opening 24.

Figure 14A:
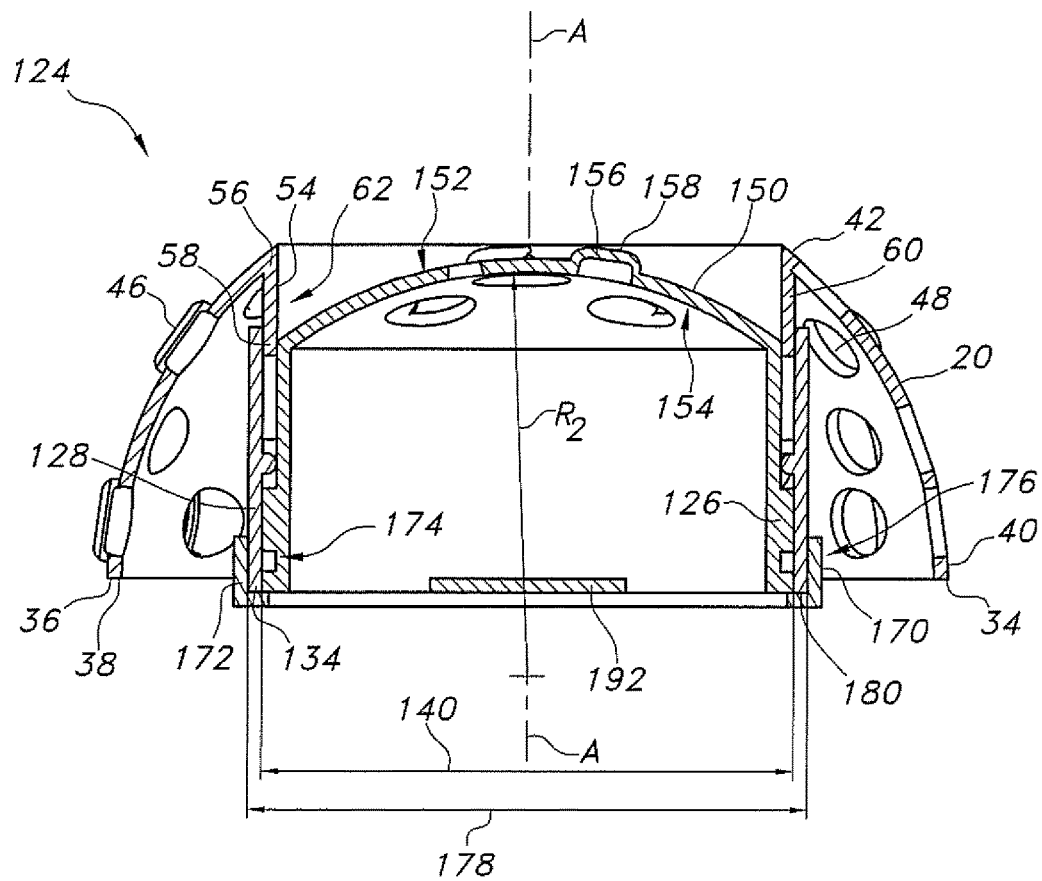
FIG. 14A is a cross-sectional view of an embodiment of a bone cutter of the present invention with the insert in a retracted position.
Figure 14B:
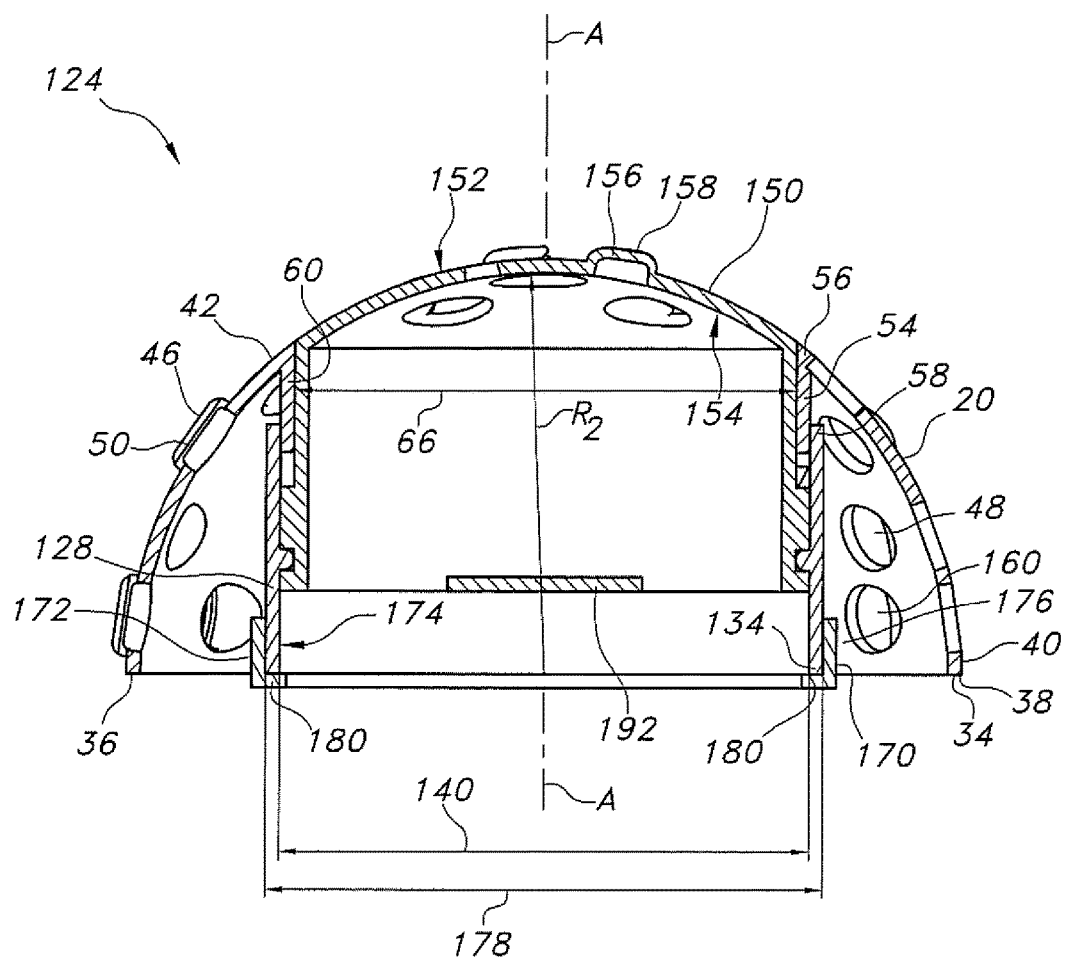
FIG. 14B is a cross-sectional view of an embodiment of a bone cutter of the present invention with the insert in an extended position.

FIGS. 11-13, 14A, and 14B, illustrate an alternative embodiment of a bone cutter 124 of the present invention. As shown, the bone cutter 124 comprises an alternate embodiment of an insert 126 and collar 128. In addition, the bone cutter 124 comprises the reamer shell 20 (FIG. 6) which comprises the shell opening 24, flange 54, and a plurality of spaced apart reamer teeth 46, as previously discussed. In an embodiment, the collar 128 has a collar proximal end 130 spaced from a collar distal end 132 that connects the reamer insert 126 to the reamer shell 20. As illustrated, the collar 128 comprises a sidewall 134 having a collar sidewall thickness that extends between diametrically opposed exterior and interior sidewall surfaces 136, 138. The collar 128 is configured in an annular shape that defines a collar interior diameter 140 that extends between opposed interior collar sidewall surfaces 138 perpendicular to the rotational axis A-A. In an embodiment, the collar 128 comprises at least two pins 142 that extend inwardly from the collar sidewall interior surface 138. In an embodiment, the collar 128 is preferably fixedly secured to the reamer shell flange 54. As illustrated in FIGS. 14A and 14B, the collar is positioned at the flange proximal end 58 such that at least a portion of the collar sidewall interior surface is in physical contact with a portion of the flange sidewall exterior surface.

FIGS. 11, 12, 14A, and 14B, illustrate an embodiment of the insert 126 of the bone cutter 124. As shown, the reamer insert 126 extends from an insert proximal end 144 to an insert distal end 146. The reamer insert 126 comprises an insert sidewall 148 having an annular shape that meets a partial hemispherically shaped insert end wall 150 at the insert distal end 146. In a preferred embodiment, the insert 126 is positioned within the reamer shell opening 24 with the insert distal end 146 oriented towards the apex 16.

Similar to the embodiment of the insert 22 of the bone cutter 10, the insert end wall 150 comprises a plurality of spaced apart insert teeth 156, each tooth having a tissue cutting surface 158. In an embodiment, each of the teeth 156 is formed from an outwardly extending portion of the insert end wall 150. In addition, each tooth 156 resides adjacent to an opening 160 that extends through the thickness of the insert end wall 150. The opening 160 allows for the removal of tissue debris during a reaming surgical procedure. The tissue cutting surface 158 formed at the distal end of each of the teeth 156 extends outwardly from the insert end wall 150 and is positioned over a respective tooth opening 160. In an embodiment, the plurality of tissue cutting surfaces 158 of the reamer insert teeth 156 are oriented about the rotational axis A-A in an opposite direction as that of the tissue cutting surfaces 50 of the reamer shell teeth 46. For example, if the tissue cutting surfaces 50 of the reamer shell teeth 46 are oriented in a clockwise direction about the rotational axis A-A, the tissue cutting surfaces 158 of the insert teeth 156 are preferably oriented in the opposite, counter-clockwise direction about the rotational axis A-A. The insert end wall 150 preferably comprises a convex structure that outwardly extends in a distal direction. The curvature of the insert end wall 150 thus allows for the insert 126 to ream a cavity having a curved surface. In an embodiment, the insert end wall 150 may comprise a convex structure having a radius of curvature $R_2$ that ranges from about 1 cm to about 5 cm.

In an embodiment, the insert annular sidewall 148 comprises at least two slots 162 that extend part-way through the sidewall 148 thickness from exterior surface 164 thereof. Each of the at least two slots 162 is preferably oriented at an angle with respect to the rotational axis A-A. In a preferred embodiment, each of the at least two slots 162 is positioned in a spiral orientation with respect to the longitudinal axis A-A extending from the insert proximal end 144 to the insert distal end 146. In an embodiment, the at least two slots 162 are configured to each receive a collar pin 142 that extends inwardly from the collar interior sidewall surface 138. A groove 166 is formed part-way through the sidewall 148 thickness from the exterior surface 164 thereof resides at the insert proximal end 144. The groove 166 forms a track on which the collar pins 142 ride. In an embodiment, the groove 166 is oriented perpendicular to the rotational axis A-A.

In an embodiment, the insert 126 is positioned within the interior of the collar 128 with each of the at least two collar pins 142 received within an insert slot 162, respectively. In an embodiment, the at least two pins 142 ride within a respective insert slot 162 that is positioned in opposition to each other. In a preferred embodiment, the pins 142 are capable of riding within the insert slot 162 in a back and forth manner from the distal insert end 146 to the groove 166 at the insert proximal end 144. As the collar pins 142 ride within the slot 162, the insert 126 rotates within the reamer shell opening 24 traveling in either a distal or proximal direction. For example, as the insert 126 is rotated in a clockwise direction, the insert may travel in a distal direction until the pins 142 exit their respective slot 162 and ride along the track formed by the groove 166 at the insert proximal end 144. In a preferred embodiment, the collar pins 142 ride along the track formed by the groove 166 so that the insert 126 is capable of 360° rotation. In an embodiment, the insert 126 may be retracted within the reamer shell 20 by rotating the insert in an opposite direction, i.e., counter-clockwise, such that the pins 142 leave the groove 166 to enter and ride within a respective slot 162 in a proximal direction so that the insert 126 retracts within the reamer shell 20.

In an embodiment, the collar 128 is secured to the reamer shell flange 54 that extends within the reamer shell 20. In an embodiment, the collar distal end 132 is secured to the reamer shell flange proximal end 58 such that rotational movement of the insert 126 within the reamer shell opening 24 is not impeded. In a preferred embodiment, the collar 128 may be secured to the reamer shell flange 54 with an adhesive or by welding the collar 100 to the flange 54. The collar 100 may be secured to the reamer shell flange 54 by a fastener (not shown). In an embodiment, the fastener (not shown) may at least partially extend through the thickness of the sidewalls of the collar 100 and reamer shell flange 54.

A band 170 (FIGS. 11, 14A, and 14B) having an annular band sidewall 172 with opposed interior and exterior sidewall surfaces 174, 176, is positioned at the collar proximal end 130. The band 170 preferably helps hold the insert 126 within the collar 100. In an embodiment, the band 170 comprises a band inner diameter 178 extending between diametrically opposed interior surfaces 174 perpendicular to the rotational axis A-A. In an embodiment, the band inner diameter 178 is greater than the outer diameter of the insert sidewall 84 and the outer diameter of the collar sidewall 134. In an embodiment illustrated in FIGS. 14A and 14B, the insert 126 is positioned within a collar opening defined by the annular collar sidewall 134 such that the insert 126 is capable of rotating therewithin. The collar 100 is secured to the flange 54 of the reamer shell 20. In an embodiment, the band 170 is positioned so that the proximal ends of the collar 100 and insert 126 fit within the interior diameter 178 of the band 170. In a preferred embodiment, the band 170 may comprise a lip 180 that is designed to support the proximal end 130 of the collar 100. In an embodiment, the lip 180 extends circumferentially about the band sidewall interior surface 174 and serves as a stop to prevent the insert 126 from separating from the reamer shell 20. In a preferred embodiment, the lip 180 extends about perpendicular to the rotational axis A-A.

Figure 10:
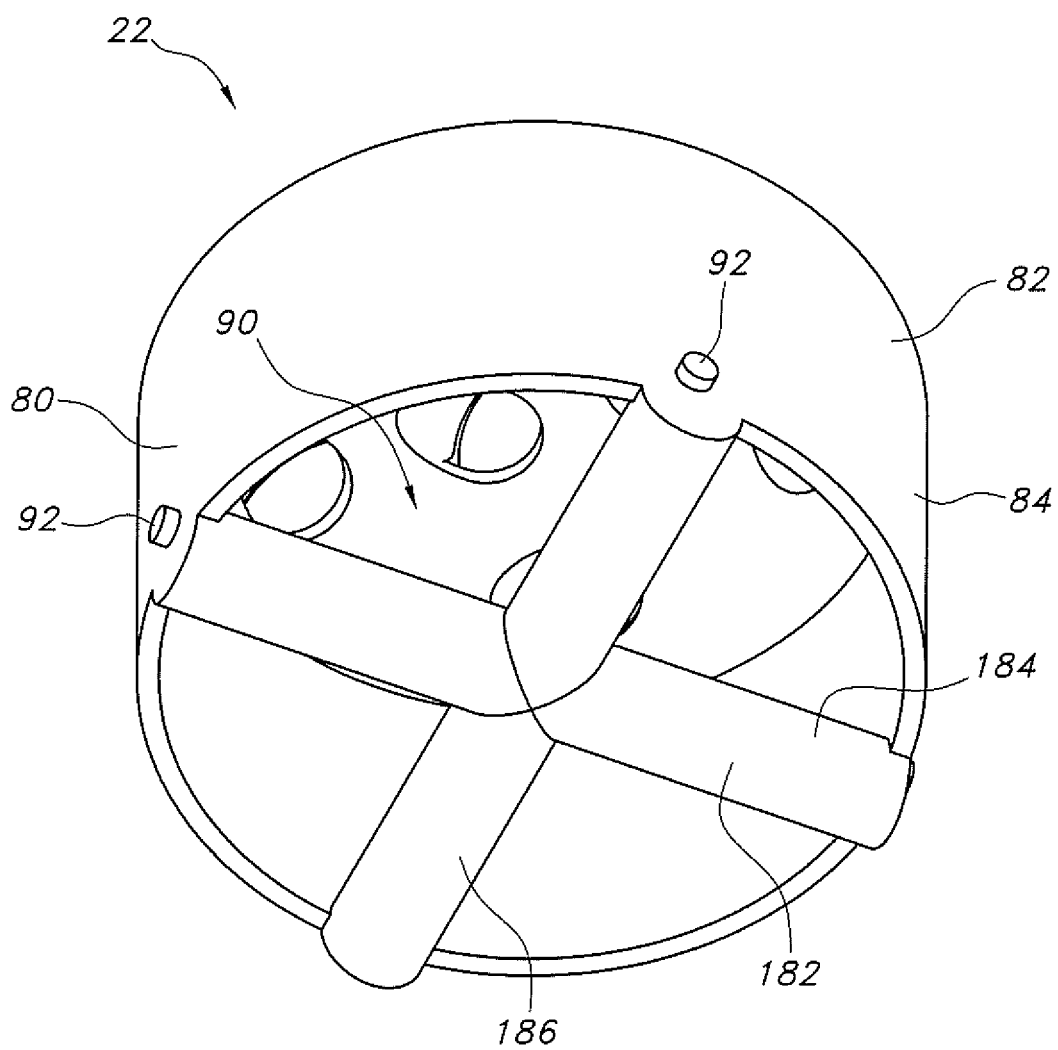
FIG. 10 illustrates an embodiment of an insert component shown from the proximal end.
Figure 11:
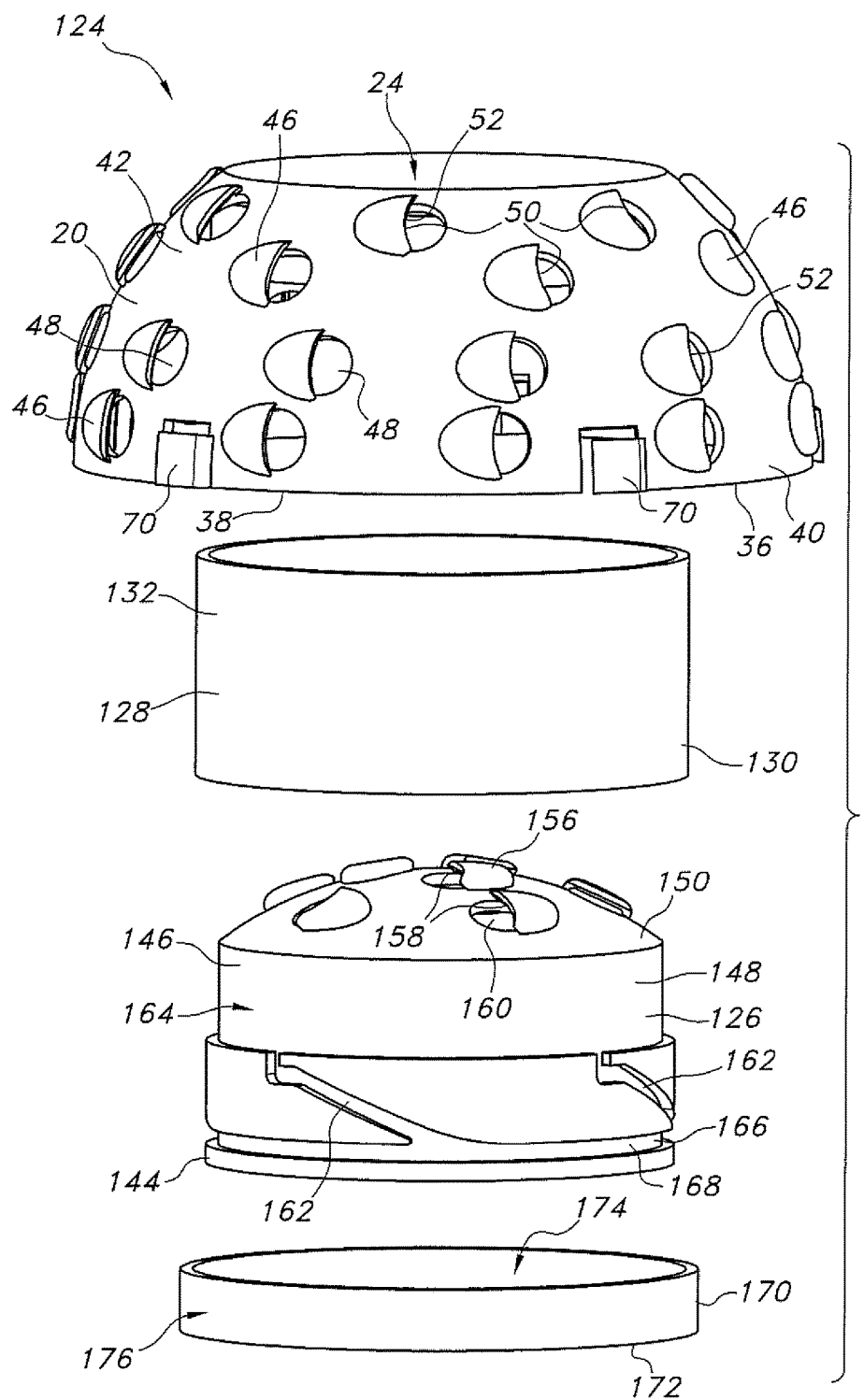
FIG. 11 shows an exploded view of an embodiment of a bone cutter of the present invention.
Figure 12:
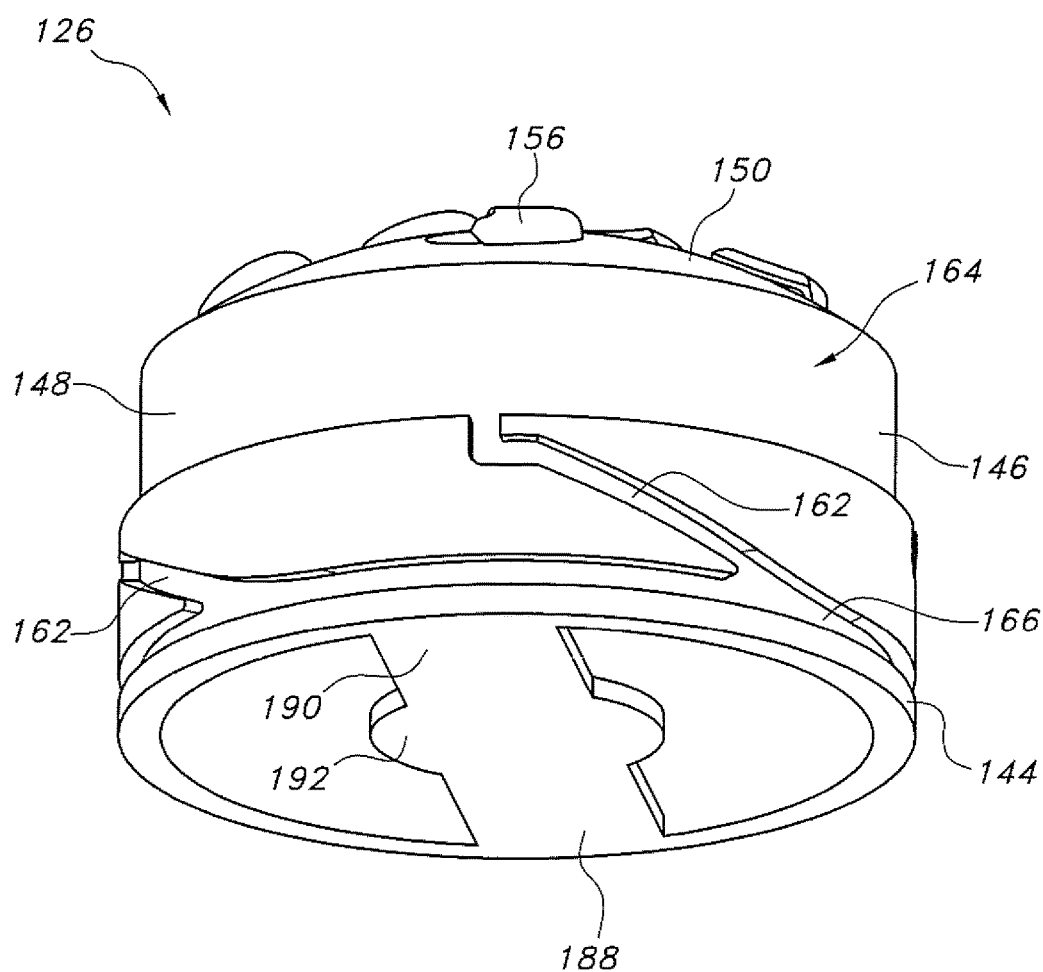
FIG. 12 illustrates an embodiment of an insert component of a bone cutter of the present invention.
Figure 13:
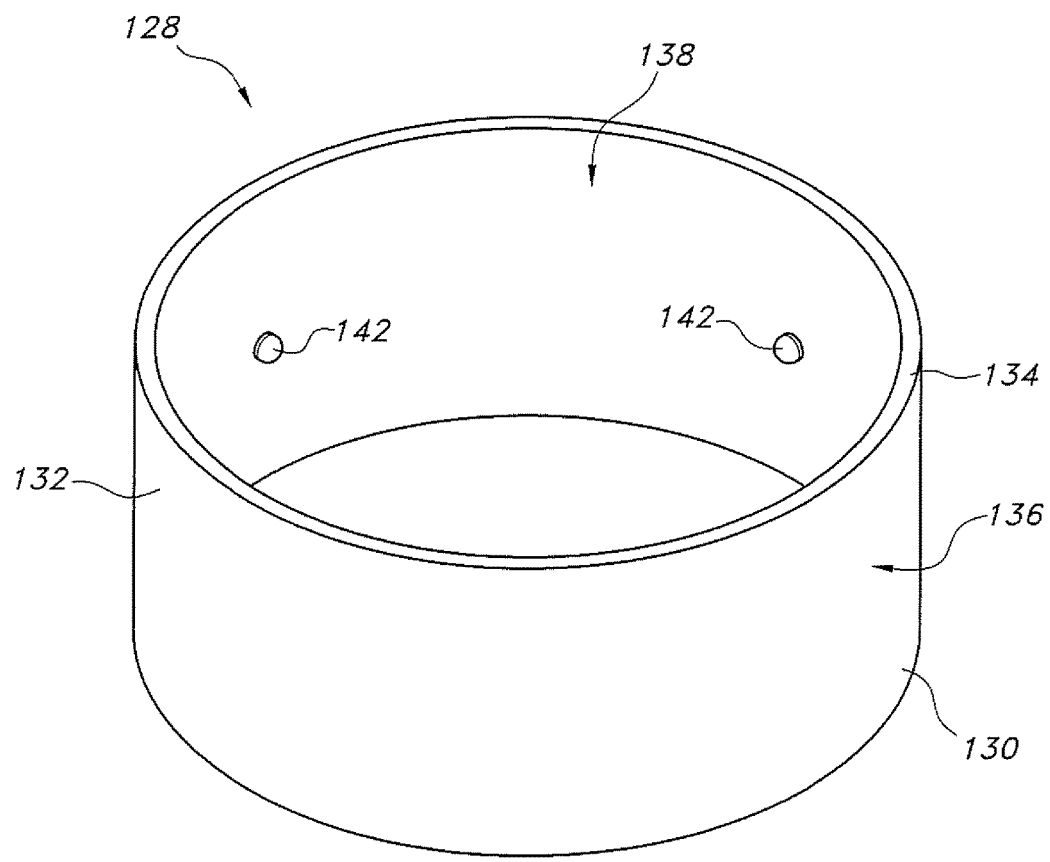
FIG. 13 illustrates an embodiment of a collar component of a bone cutter of the present invention.

The bone cutters 10, 124 of the present invention are designed to be connectable to a driver shaft (not shown). FIGS. 10 and 12 illustrate two different embodiments of a driver interface that connects with the driver shaft of a rotary power tool to thereby impart rotational movement to the bone cutters 10, 124. As shown in the embodiment of FIG. 10, a driver interface 182 is of a crossbar design. Specifically, the driver interface 182 comprises a first bar 184 and second bar 186 that are orientated perpendicularly to each other. In the embodiment shown, the bars 184, 186 are of a curved cross-section perpendicular to their length. However, other cross-sectional geometries may be used such as, but not limited to, a rectangular or a triangular cross-section. As illustrated, the bars 184, 186 are positioned within the base portion of the insert 22, 126, the respective insert annular sidewalls 84, 148 extending circumferentially around the bars 184, 186.

FIG. 12 illustrates an alternative embodiment of a driver interface 188. As shown, the driver interface 188 comprises a bar and boss interface. This driver interface 188 comprises a bar portion 190 extending to a boss 192. The boss 192 has opposed semi-circular sides meeting the bar portion 190. Similar to the previous crossed bar driver interface 182, the bar and boss interface 188 may extend across the diameter of the base portion of the insert 22, 126.

FIGS. 16A and 16B illustrate embodiments of the operation of the bone cutters 10, 124, of the present invention. In operation, either embodiment of the bone cutter 10, 124 is preferably positioned within an opening of the body near the acetabulum with the insert 22, 126 in a retracted positioned within the interior of the shell 20. As illustrated in FIGS. 2, 4A, 14A, and 16A, in a preferred embodiment, the retracted position is defined as when the insert tissue cutting surfaces 96, 158 are positioned within the shell interior below the shell opening perimeter. Once positioned within the body, the shell 20 of the bone cutter 10, 124 is rotated in the direction of the reamer shell tissue cutting surfaces 96, 158, in either a clockwise or counterclockwise direction. This allows for the reamer shell to cut tissue and/or bone such as the acetabular roof 28 and acetabular labrum 30.

Once the acetabular roof and labrum have been sufficiently reamed, the reamer shell 20 is rotated in the opposite direction to thereby anchor the reamer shell within surrounding tissue and/or bone. After the shell 20 is anchored, the insert 22, 126 is continued to be rotated in the same direction to extend the insert tissue cutting teeth 94, 156 from within the shell interior. In a preferred embodiment, the insert is rotated in the opposite direction of the orientation of the shell cutting teeth 46 to extend the insert cutting teeth 94, 156 past the reamer shell opening 24. Once extended, the insert 22, 126 is continued to be rotated so that acetabular floor and fossa are adequately reamed to the appropriate diameter. The reamer insert is then rotated in the opposite direction to retract the insert cutting teeth 94, 156 into the reamer shell interior. The bone cutter anchors 70 are dislodged from the surrounding bone and tissue and the bone cutter 10, 124 is removed from the body.

In a preferred embodiment, the reamer shell 20, inserts 22, 126, collars 100, 128 and band 170 are composed of a biocompatible material. More specifically, at least one of the reamer shell 20, inserts 22, 126, collars 100, 128 and band 170 may be composed of a biocompatible polymer, metal or ceramic material. Examples of such polymeric materials include, but are not limited to, acrylonitrile butadiene styrene (ABS), polyacrylamides (PARA), polyetherimide (PEI), and polyetheretherketone (PEEK). In addition, examples of metallic materials include, but are not limited to, stainless steel, titanium, MP35N, and a biocompatible metal.

While the preferred embodiments of the cutting device and methods have been described in reference to the environment in which they were developed, they are merely illustrative of the principles of the inventions. Other embodiments and configurations may be devised without departing from the spirit of the inventions and the scope of the appended claims.

What is claimed is:

1. An orthopedic bone cutter, comprising:
    a) a cutting shell having a base and a shell sidewall with a curvature that comprises at least a portion of a hemisphere, the cutting shell extending from said base towards an imaginary apex, an opening having an opening perimeter extends through the shell sidewall at the imaginary apex to a cutting shell interior, a rotational axis extends through the imaginary apex, the cutting shell being rotatable about the rotational axis;
    b) a flange having an annular flange sidewall defining a flange opening, the flange extending from the shell opening perimeter at a flange distal end to a flange proximal end positioned within the shell interior;
    c) a plurality of outwardly extending and spaced apart shell cutting teeth;
    d) an insert extending from an insert proximal end to an insert distal end, the insert comprising an annular insert sidewall that meets an insert end wall at the insert distal end, the insert positioned within the flange opening along the rotational axis, wherein the insert distal end faces the imaginary apex;
    e) a plurality of outwardly extending and spaced apart insert cutting teeth; and
    f) wherein the insert is capable of rotational and axial movement about the rotational axis.

2. The orthopedic bone cutter of claim 1 wherein rotation of the insert causes the insert to move axially along the rotational axis either in a distal direction towards the imaginary apex or in a proximal direction within cutting shell interior.

3. The orthopedic bone cutter of claim 1 wherein the shell cutting teeth and the insert cutting teeth are in opposite directions.

4. The orthopedic bone cutter of claim 1 wherein the insert end wall comprises a convex shape that outwardly projects in a distal direction.

5. The orthopedic bone cutter of claim 1 wherein the insert end wall has a curvature extending in a distal direction, wherein the curvature has a radius of curvature that ranges from 1 cm to 5 cm originating from within the shell interior.

6. The orthopedic bone cutter of claim 1 further comprising a collar that extends from a collar proximal end to a collar distal end, the collar having an annular collar sidewall with opposed interior and exterior collar sidewall surfaces defining a collar opening, wherein the insert is positioned within the collar opening with the insert distal end facing the apex, and wherein the collar comprises:
    a) at least one slot having spaced apart slot proximal and distal ends, wherein the slot distal end is spaced from the collar distal end, the slot proximal end is spaced from the collar proximal end; and
    b) a groove orientated about perpendicular to the rotational axis formed at least partially within the collar sidewall from the interior surface, wherein the slot distal end meets the groove, and wherein the groove extends circumferentially about the annular collar sidewall at the collar distal end.

7. The orthopedic bone cutter of claim 6 wherein at least one pin extends outwardly from the insert sidewall exterior surface, wherein the at least one pin is received within a respective collar slot and is capable of riding therewithin.

8. The orthopedic bone cutter of claim 1 wherein the cutting shell or insert is composed of a material selected from the group consisting of acrylonitrile butadiene styrene (ABS), polyacrylamides (PARA), polyetherimide (PEI), polyetheretherketone (PEEK), a biocompatible polymeric material, and combinations thereof.

9. The orthopedic bone cutter of claim 1 further comprising a shaft driver interface having a bar and boss configuration or a cross bar configuration positioned at the insert proximal end.

10. The orthopedic bone cutter of claim 1 further comprising a collar that extends from a collar proximal end to a collar distal end having an annular collar sidewall with opposed interior and exterior collar sidewall surfaces defining a collar opening, at least one pin extends from the collar annular sidewall interior surface towards the rotational axis, the collar distal end being secured to the flange proximal end, wherein the insert is positioned within the collar opening, the insert capable of rotational and axial movement therewithin.

11. The orthopedic bone cutter of claim 10 wherein at least one slot extends at least partially within the insert sidewall from an exterior insert surface, the at least one slot extending from a slot proximal end spaced from the insert proximal end to a slot distal end spaced from the insert distal end, wherein the at least one slot is configured to receive the at least one pin.

12. The orthopedic bone cutter of claim 10 wherein a groove is formed at least partially within the insert sidewall from an exterior insert surface, the groove extending circumferentially about the annular insert sidewall at the insert proximal end, wherein the groove forms a track configured to receive the at least one pin.

13. The orthopedic bone cutter of claim 10 wherein a band comprising an annular band sidewall extending from a band proximal end to a band distal end having opposed interior and exterior sidewall surfaces is positioned at the collar proximal end, wherein the band comprises a lip that extends from the interior sidewall surface towards the rotational axis at the band proximal end.

14. The orthopedic bone cutter of claim 1 further comprising an anchor that outwardly extends from an exterior surface of the cutting shell, the anchor having an anchor tissue cutting surface.

15. The orthopedic bone cutter of claim 14 wherein the anchor tissue cutting surface is oriented in an opposite direction as the shell cutting teeth.

16. The orthopedic bone cutter of claim 15 wherein the shell comprises an anchor opening that extends through the shell sidewall at the shell proximal end, wherein at least a portion of the anchor tissue cutting surface extends over the opening.

17. An orthopedic bone cutter, comprising:
a) a cutting shell having a base and a shell sidewall with curvature that comprises at least a portion of a hemisphere, the cutting shell, extending from said base defining a lower perimeter to an intermediate edge defining an intermediate perimeter located on an imaginary intermediate plane that is spaced from and positioned between an imaginary apex and the lower edge, wherein the lower perimeter of the lower edge is greater than the intermediate perimeter of the intermediate edge, the cutting shell being rotatable about a rotational axis;
b) a flange having an annular flange sidewall that defines a flange opening that extends from a flange distal end at the intermediate edge to a flange proximal end extending towards the shell lower edge;
c) a plurality of outwardly extending and spaced apart cutting shell teeth;
d) an insert having an insert proximal end that extends to an insert distal end, wherein the insert comprises an annular insert sidewall wall that meets an insert end wall at the insert distal end, the insert positioned within the flange opening along the rotational axis, wherein the insert distal end faces the imaginary apex;
e) a plurality of outwardly extending and spaced apart insert cutting teeth; and
f) wherein the insert is capable of rotational and axial movement about the rotational axis.

18. The orthopedic bone cutter of claim 17 wherein rotation of the insert causes the insert to move axially in distal direction towards the imaginary apex or in a proximal direction towards the shell lower edge.

19. The orthopedic bone cutter of claim 17 wherein the shell cutting teeth and the insert cutting teeth are oriented in opposite directions.

20. The orthopedic bone cutter of claim 17 wherein the insert end wall comprises a convex shape that outwardly projects in a distal direction.

21. The orthopedic bone cutter of claim 17 further comprising a collar that extends from a collar proximal end to a collar distal end, the collar having an annular collar sidewall with opposed interior and exterior collar sidewall surfaces defining a collar opening, wherein the insert is positioned within the collar opening with the insert distal end facing the apex, and wherein the collar comprises:
a) at least one slot having spaced apart slot proximal and distal ends, wherein the slot distal end is spaced from the collar distal end, the slot proximal end is spaced from the collar proximal end; and
b) a groove orientated about perpendicular to the rotational axis formed at least partially within the collar sidewall from the interior surface, wherein the slot distal end meets the groove, and wherein the groove extends circumferentially about the annular collar sidewall at the collar distal end.

22. The orthopedic bone cutter of claim 21 wherein a pin extends outwardly from the insert sidewall exterior surface, and wherein the pin is received within the collar slot and is capable of riding therewithin.

23. The orthopedic bone cutter of claim 17 further comprising a shaft driver interface having a bar and boss configuration or a cross bar configuration positioned at the insert proximal end.

24. The orthopedic bone cutter of claim 17 further comprising a collar that extends from a collar proximal end to a collar distal end, the collar comprises an annular collar sidewall having opposed interior and exterior collar sidewall surfaces that defines a collar opening, at least one pin extends from the collar annular sidewall interior surface towards the longitudinal axis, the collar distal end being secured to the flange proximal end, wherein the insert is positioned within the collar opening capable of rotational and axial movement therewithin.

25. The orthopedic bone cutter of claim 24 wherein at least one slot extends at least partially within the insert sidewall from the exterior sidewall surface, the at least one slot extending from a slot proximal end spaced from the insert proximal end to a slot distal end spaced from the insert distal end, wherein the at least one pin is received within a respective slot.

26. The orthopedic bone cutter of claim 24 wherein a groove is formed at least partially within the insert sidewall from the exterior sidewall surface, the groove extending circumferentially about the annular insert sidewall at the insert proximal end, wherein the groove forms a track configured to receive the at least one pin.

27. The orthopedic bone cutter of claim 24 wherein a band comprising an annular band sidewall extending from a band proximal end to a band distal end having opposed interior and exterior sidewall surfaces is positioned at the collar proximal end, wherein the band comprises a lip that extends from the interior sidewall surface towards the rotational axis at the band proximal end.

28. The orthopedic bone cutter of claim 17 further comprising an anchor that outwardly extends from an exterior surface of the reamer shell, the anchor having an anchor tissue cutting surface.

29. The orthopedic bone cutter of claim 28 wherein the anchor tissue cutting surface is oriented in an opposite direction as the shell cutting teeth.

30. The orthopedic bone cutter of claim 29 wherein the shell comprises an anchor opening that extends through the shell sidewall at the shell proximal end, wherein at least a portion of the anchor tissue cutting surface extends over the opening.

* * * * *